United States Patent
Watanabe et al.

(10) Patent No.: US 7,153,999 B2
(45) Date of Patent: Dec. 26, 2006

(54) PRODUCTION OF DIMETHYLOLCARBOXYLIC ACID

(75) Inventors: Toshio Watanabe, Okayama (JP); Atsushi Iwamoto, Okayama (JP); Soemu Miyashita, Okayama (JP); Masafumi Watanabe, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 1040 days.

(21) Appl. No.: 10/051,025

(22) Filed: Jan. 22, 2002

(65) Prior Publication Data

US 2002/0107417 A1 Aug. 8, 2002

(30) Foreign Application Priority Data

Feb. 2, 2001  (JP) ........................ 2001-026304

(51) Int. Cl.
*C07C 59/10* (2006.01)

(52) U.S. Cl. ...................................... 562/587
(58) Field of Classification Search .................. 562/587
See application file for complete search history.

(56) References Cited

PUBLICATIONS

Heinonen, et al., Synthesis of Achiral α,α–Disubstituted β–Alanines, and Their Use in Construction of Libraries of β–Peptide Conjugates of N–2–alkyl–1,2,3,4–Tetrahydroisoquinolines on a Solid Support, Department of Chemistry, University of Turku, FIN–20014 Turku, Finland, pp. 7613–7624.

Werle, et al., Synthese der Dimethylolessigsäure, Anwendungstechnik und Forschung Chemie der Degussa AG, ZN Wolfgang, Postfach 1345, D–6450 Hanau 1, pp. 944–946.

Green, et al., *Protective Groups In Organic Synthesis* (2d Ed. 1991), pp. 119–120.

English abstract of JP 06–192169 (Jul. 12, 1994), AN 1994–260465 (Database WPI).

European Search Report for No. 02001387, completed Dec. 16, 2002.

*Primary Examiner*—Paul J. Killos
(74) *Attorney, Agent, or Firm*—Antonelli, Terry, Stout & Kraus, LLP

(57) ABSTRACT

In the method of the present invention, a dimethylolcarboxylic acid is produced by reacting a trimethylolalkane and formaldehyde to prepare a cyclic formal having a formal protecting group, followed by the oxidation of the cyclic formal by using nitric acid as an oxidizing agent to prepare a cyclic carboxylic acid which is then subjected to cleavage to remove the formal protecting group. The formal protecting group protects two of the methylol groups against the oxidation to enable the production of the dimethylolcarboxylic acid with a high selectivity.

17 Claims, No Drawings

PRODUCTION OF DIMETHYLOLCARBOXYLIC ACID

BACKGROUND OF THE INVENTION

1. Field of the Invention

The present invention relates to a method for producing a dimethylolcarboxylic acid such as dimethylolbutanoic acid which is useful as a material for producing an aqueous polyurethane resin, a polyester resin, an alkyd resin, a polycarbonate resin, a plasticizer, a lubricating oil, a surfactant, a base material for cosmetics, a reactive monomer, etc.

2. Description of the Prior Art

As a general method for producing dimethylolbutanoic acid, known is a direct oxidation method of the methylol group of trimethylolpropane (hereinafter referred to as "TMP"). The oxidation method includes chromium acid oxidation (Jones oxidation), oxidation using aluminum alkoxide (Openauer oxidation), oxidation using a noble metal such as Pt and Pd as disclosed in Japanese Patent Application Laid-Open No. 6-192169, etc.

In another method disclosed in U.S. Pat. No. 6,072,082, dimethylolbutanoic acid is obtained through the steps of producing 2,2-dimethylolbutanal, producing dimethylolbutanoic acid, and recovering dimethylolbutanoic acid. In the production process of 2,2-dimethylolbutanal, n-butylaldehyde (herein after referred to as "NBAL") and formaldehyde are subjected to aldol condensation in the presence of a basic catalyst to produce 2,2-dimethylolbutanal. In the production process of dimethylolbutanoic acid, 2,2-dimethylolbutanal thus obtained is oxidized by hydrogen peroxide to dimethylolbutanoic acid. In the recovery step, dimethylolbutanoic acid is generally collected through the steps of neutralizing a salt of dimethylolbutanoic acid thus obtained by acid, extracting the liberated dimethylolbutanoic acid by ketone, and crystallizing dimethylolbutanoic acid.

The direct oxidation such as Jones oxidation and Oppenauer oxidation is excellent in oxidation efficiency, but not suitable as the industrial method because it requires a harmful compound, it by-produces a harmful waste, and it complicates the reaction steps. The oxidation by noble metal proceeds slowly under relatively mild conditions, and it requires a step for recovering the carboxylic acid by acid precipitation because the oxidation should be carried out under basic conditions to form a salt of the objective dimethylolbutanoic acid. In addition, since wastes such as sodium sulfate are produced, this oxidation method is not industrially practicable.

TMP has three chemically equivalent methylol groups. If TMP is freely oxidized, the by-production of a dicarboxylic acid and a tricarboxylic acid in addition to the objective monocarboxylic acid is unavoidable. To avoid this problem, a method for oxidizing TMP in a low conversion is known. This method, however, is disadvantageous in view of production efficiency and requires an additional step for removing non-reacted TMP, by-produced dicarboxylic acid, etc.

In the method by the oxidation of an alkanal, NBAL and formaldehyde are subjected to aldol condensation to produce 2,2-dimethylolbutanal. However, 2,2-dimethylolbutanal is thermally instable to reduced the yield based on NBAL. In addition, since the aldol condensation requires a basic catalyst such as sodium hydroxide, dimethylolbutanoic acid should be precipitated from a solution by acid during its purification. This makes the method industrially disadvantageous.

SUMMARY OF THE INVENTION

An object of the present invention is to provide a method for producing a dimethylolcarboxylic acid such as dimethylolbutanoic acid from a trimethylolalkane (hereinafter referred to as TMA) with high selectivity.

As a result of extensive study on the conventional methods of producing dimethylolbutanoic acid, the inventors have found that the objective dimethylolcarboxylic acid is produced in high selectivity by a method comprising a step of reacting TMA and formaldehyde in the presence of an acidic catalyst to produce a cyclic formal (hereinafter referred to as "CMF"); a step of oxidizing the methylol group of the cyclic formal using nitric acid as an oxidizing agent to produce a cyclic carboxylic acid (hereinafter referred to as "CBA"); and a step of cleaving the formal protecting group of the cyclic carboxylic acid.

Thus, the present invention provides a method for producing a dimethylolcarboxylic acid represented by the following formula 1:

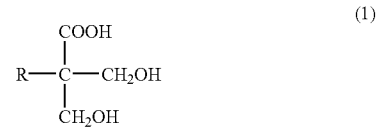

wherein R is a $C_1$–$C_4$ alkyl group,
which comprises:
a step A for reacting trimethylolalkane represented by the following formula 2:

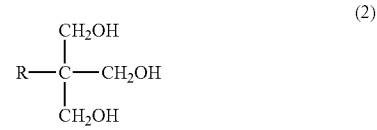

wherein R is as defined above,
with formaldehyde in the presence of an acidic catalyst, thereby producing a cyclic formal represented by the following formula 3 having a formal protecting group:

wherein R is as defined above;
a step B for oxidizing the cyclic formal produced in the step A using nitric acid as an oxidizing agent in the presence or absence of a catalyst, thereby producing a cyclic carboxylic acid represented by the following formula 4

wherein R is as defined above; and
a step C for cleaving the formal protecting group of the cyclic carboxylic acid produced in the step B to the dimethylolcarboxylic acid of the formula 1 in the presence of an acidic catalyst.

DETAILED DESCRIPTION OF THE INVENTION

The objective dimethylolcarboxylic acid of the present invention is represented by the following formula 1:

(1)

In the formula 1, R is a $C_1$–$C_4$ alkyl group, preferably methyl group or ethyl group. Preferred dimethylolcarboxylic acids are dimethylolpropanoic acid and dimethylolbutanoic acid, with dimethylolbutanoic acid being more preferred.

Step A: Production of CMF

In the method of the present invention, as shown in the following reaction scheme:

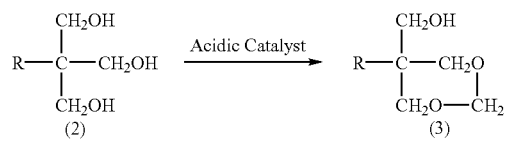

wherein R is as defined above, a trimethylolalkane 2 (TMA) is reacted with formaldehyde in the presence of an acidic catalyst to produce a cyclic formal 3 (CMF), thereby protecting two of the three methylol groups of TMA by a formal protecting group against the oxidation of the next step. The selection of the protecting group for tow methylol groups of TMA is important in the present invention. Various kinds of compounds such as ester, ether and aldehyde are generally used for protecting the methylol groups. In the present invention, it is particularly suitable to form a cyclic acetal by formaldehyde, because the cyclic acetal protection stands stable against the oxidation by nitric acid.

In the present invention, either a formaldehyde aqueous solution or a solid paraformaldehyde may be used as formaldehyde for producing CMF. Formaldehyde is used 0.1 to 1.5 mol per one mole of the starting TMA. CMF is produced in higher selectivity by conducting the reaction in TMA excess rather than in formaldehyde excess because the by-production can be minimized. Therefore, the reaction is carried out preferably in excess of TMA by using formaldehyde 0.6 to 0.9 mol per one mole of TMA (theoretical molar ratio=1.0). To omit the step for recovering the excess starting compound, formaldehyde is more preferably used 0.9 to 1.1 mol per one mole of TMA.

As the acidic catalyst for use in the production of CMF, usable are any of a mineral acid such as hydrochloric acid and phosphoric acid, an organic acid such as formic acid, p-toluenesulfonic acid and methanesulfonic acid, and a mixture thereof, with phosphoric acid being preferred for industrial use. The acidic catalyst is used 0.1 to 2.0% by weight based on the starting TMA. The amount of the acidic catalyst is suitably selected from the above range according to the reaction conditions so as to produce the objective CMF in a high selectivity while minimizing the production of by-product.

The reaction for producing CMF may be carried out in the presence of a solvent, although the reaction proceeds without the use of a solvent. Examples of the solvent include ethers such as ethyl cellosolve and dioxane, aromatic hydrocarbons such as toluene and xylene, and aliphatic hydrocarbons such as hexane and heptane. During the production of CMF, water is generated in amounts equimolar with CMF. Water is also introduced to the reaction system as a solvent for the starting material when a formaldehyde aqueous solution is used as the starting material. By removing such water from the reaction system as an azeotropic mixture with the solvent, the reaction can be proceeded more efficiently.

The production of CMF may be carried out in either batch-wise manner or continuous manner at ordinary pressure or increased pressure. When carried out at ordinary pressure, the reaction temperature is 60 to 100° C. depending on the amount of the catalyst, and the reaction time is 30 to 300 min. When carried out at a pressure of 0 to 0.3 MPa, the reaction time can be reduced to 10 to 60 min by carrying out the reaction at 100 to 150° C.

After removing water, the reaction liquid of TMA-excess reaction is vacuum-distilled to separate purified CMF. The excess TMA is recovered as a bottom product. When the reaction is carried out in excess of formaldehyde, the excess formaldehyde is recovered simultaneously with the removal of water, and then, the reaction liquid is vacuum-distilled to separate purified CMF.

Step B: Oxidation of CMF

One of the characteristic features of the present invention is the use of nitric acid as an oxidizing agent for oxidizing the methylol group. By conducting the oxidation under acidic conditions, the separation of the objective dimethylolcarboxylic acid needs no acid precipitation. In addition, by-produced NO is recycled as nitric acid through recovery and air-oxidation.

The purified CMF obtained in the step A is oxidized to a cyclic carboxylic acid 4 (CBA) using nitric acid as the oxidizing agent in the presence or absence of a catalyst according to the following reaction scheme:

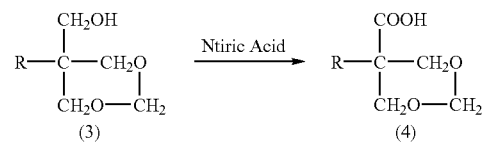

wherein R is as defined above.

Nitric acid is used 1.5 to 3.0 mol, preferably 1.9 to 2.3 mol per one mol of CMF (theoretical molar ratio=2.0). Nitric acid is used as an aqueous solution of 10 to 63 wt % concentration. To proceed the reaction more efficiently, a catalyst such as sulfuric acid, sodium nitrite, ammonium vanadate and vanadium(V) oxide may be used.

The oxidation of CMF may be carried out in either batch-wise manner or continuous manner. The reaction temperature and time depends on the concentration of the aqueous solution of nitric acid being used, and preferably 30 to 100° C. for 1 to 5 h. After the oxidation, the non-reacted nitric acid is distilled simultaneously with the removal of water present in the reaction liquid, thereby obtaining CBA.

Step C: Cleavage of protecting group of CBA

The protecting group remaining in CBA obtained by the oxidation is cleaved by hydrogenation or heating in water or alcoholic solvent to give the objective dimethylolcarboxylic acid 1 according to the following scheme:

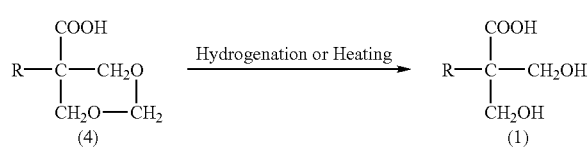

wherein R is as defined above.

The cleavage by hydrogenation is carried out in the presence of a noble metal catalyst such as Pt and Pd, a nickel catalyst or a copper-chromium catalyst. The hydrogenation may be carried out in either batch-wise manner or continuous manner. Although depending on the catalyst used, the hydrogen pressure is 0.2 to 15.0 MPa. CBA is hydrogenated as an aqueous solution of 5 to 50 wt % concentration, preferably 10 to 20 wt % concentration at 120 to 200° C. for 30 min to 5 h.

The cleavage by heating is carried out in the presence of an acidic catalyst using water or a $C_1$–$C_4$ alcohol such as methanol and ethanol. Examples of the acidic catalyst include mineral acids such as phosphoric acid and sulfuric acid and organic acids such as p-toluenesulfonic acid and methanesulfonic acid, with sulfuric acid being particularly preferred. Although depending on the heating conditions, the acidic catalyst is usually used from 500 ppm to 5 wt % based on CBA. The heating is carried out at 60 to 200° C. for 1 to 5 h. When the reaction is carried out at 100° C. or higher, it is preferable to conduct the reaction under pressure (0 to 0.5 MPa) with refluxing. When using the $C_1$–$C_4$ alcohol such as methanol and ethanol as the solvent, the reaction is proceeded preferably by removing a low boiling substance such as methylal that is generated by heat decomposition from the reaction system by fractional distillation during heat refluxing.

After removing water by evaporation, the dimethylolcarboxylic acid obtained by the cleavage of the formal protecting group of CBA is crystallized from a solvent, for example, ketones such as methyl isobutyl ketone, esters such as ethyl acetate or alcohols such as butanol.

The present invention will be described in further detail by way of the following examples. However, it should be noted that the following examples are not intended to limit the scope of the invention thereto.

EXAMPLE 1
(Synthesis of CMF)

Into a 1-L vessel, were charged 710.2 g (5.30 mol) of TMP, 278.3 g (3.71 mol) of a 40% aqueous solution of formaldehyde and 10 g of p-toluenesulfonic acid as a catalyst. The mixture was heated to 100° C. under stirring. Thereafter, the reaction was allowed to proceed for one hour under refluxing at 100° C. Then, the temperature was raised to 150° C. while removing water by distillation. The amount of water distilled was 252.6 g. The resultant 745.9 g of reaction liquid was vacuum-distilled to obtain 545.9 g (3.79 mol) of CMF distillate. The residue (200 g) in the vessel contained 83% TMP EXAMPLE 2
(Oxidation of CMF)

Into 230 g (2.19 mol) of a 60% concentrated nitric acid in a 500-mL vessel, 139 g (0.952 mol) of CMF prepared in Example 1 was added dropwise over 30 min. The liquid was cooled during the dropwise addition so as to keep the temperature at 40° C. After completing the addition, the mixture was further kept at 40° C. for 60 min. The resultant reaction liquid was analyzed by gas chromatography, and it was confirmed that the starting CMF was substantially all exhausted and the peak area of CBA was 99.9% of the total peak area of the gas chromatogram. The reaction liquid was heated to 100° C. to remove the remaining nitric acid and water, thereby obtaining crude CBA.

EXAMPLE 3
(Cleavage of CBA by Hydrogenation)

Into a 500-mL pressure vessel, were placed 50 g (0.342 mol) of CBA prepared in Example 2, 150 g of water and 2 g of a 5% Pd/C catalyst, and the pressure was raised to 1.0 MPa by introducing hydrogen. The temperature was raised to 200° C. and kept there for 2 h. The resultant reaction liquid was analyzed by gas chromatography, and it was confirmed that the peak area of dimethylolbutanoic acid was 85% of the total area of the gas chromatogram. After removing water from the reaction liquid, dimethylolbutanoic acid of 99.9% purity was obtained by crystallization from 100 g of methyl isobutyl ketone.

EXAMPLE 4
(Cleavage of CBA by heating)

After diluting 50 g (0.342 mol) of CBA prepared in Example 2 with 150 g of water, the resultant liquid was fed into a pressure distillation column at 0.3 MPa. The distillation was conducted at a bottom temperature of 150° C., rejecting 50 g of the distillate and collecting 100 g of the bottom product. The gas chromatographic analysis of the bottom product showed that the peak area of dimethylolbutanoic acid was 65% of the total peak area of the gas chromatogram.

Comparative Example 1

Into a 500-mL vessel, was added 230 g (2.19 mol) of a 60% concentrated nitric acid, to which 128 g (0.955 mol) of TMP was added dropwise over 30 min. During the dropwise addition, the temperature was kept at 40° C. by cooling. After completing the addition, the resultant liquid was further kept at 40° C. for 60 min. The result of gas chromatographic analysis showed that TMP was completely exhausted and the peak area was 15% for dimethylolbutanoic acid, 30% for dicarboxylic acid and 50% for tricarboxylic acid, each based on the total peak area of the gas chromatogram. Therefore, dimethylolbutanoic acid of high purity could not obtained by crystallization.

As seen from the above examples, the method of the present invention produces dimethylolcarboxylic acid with a good selectivity by reacting trimethylolalkane and formaldehyde in the presence of an acidic catalyst to prepare a cyclic formal; oxidizing the cyclic formal using nitric acid as the oxidizing agent to prepare a cyclic carboxylic acid; and then, cleaving the protecting group remaining in the cyclic carboxylic acid. In addition, since no acid precipitation is needed, the waste such as sodium sulfate is not produced. Therefore, the present invention is of great industrial value.

What is claimed is:

1. A method for producing a dimethylolcarboxylic acid represented by the following formula 1:

wherein R is a $C_1$–$C_4$ alkyl group, which comprises:

a step A for reacting trimethylolalkane represented by the following formula 2:

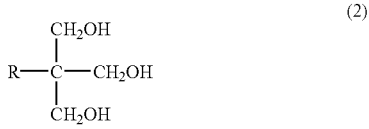

wherein R is as defined above,
with formaldehyde in the presence of an acidic catalyst, thereby producing a cyclic formal represented by the following formula 3 having a formal protecting group:

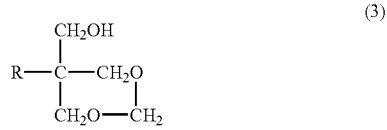

wherein R is as defined above;
a step B for oxidizing the cyclic formal produced in the step A using nitric acid as an oxidizing agent in the presence or absence of a catalyst, thereby producing a cyclic carboxylic acid represented by the following formula 4:

wherein R is as defined above; and
a step C for cleaving the formal protecting group of the cyclic carboxylic acid produced in the step B to obtain the dimethylolcarboxylic acid of the formula 1.

2. The method according to claim 1, wherein R is methyl group or ethyl group.

3. The method according to claim 1, wherein formaldehyde is used in an amount of 0.1 to 1.5 mol per one mol of the trimethylolalkane.

4. The method according to claim 1, wherein the acidic catalyst used in the step A is at least one acid selected from the group consisting of hydrochloric acid, phosphoric acid, sulfuric acid, formic acid, p-toluenesulfonic acid and methanesulfonic acid.

5. The method according to claim 1, wherein the acidic catalyst of the step A is used in an amount of 0.1 to 2.0% by weight based on the trimethylolalkane.

6. The method according to claim 1, wherein the step A is carried out at 60 to 100° C. for 30 to 300 min under ordinary pressure.

7. The method according to claim 1, wherein the step A is carried out at 100 to 150° C. for 10 to 60 min under 0 to 0.3 MPa.

8. The method according to claim 1, wherein the catalyst of the step B is at least one compound selected from the group consisting of sulfuric acid, sodium nitrite, ammonium vanadate and vanadium(V) oxide.

9. The method according to claim 8, wherein nitric acid is used in an amount of 1.5 to 3.0 mol per one mol of the cyclic formal.

10. The method according to claim 1, wherein the step B is carried out at 30 to 100° C. for 1 to 5 h.

11. The method according to claim 1, wherein the cleavage of the formal protecting group of the cyclic carboxylic acid in the step C is carried out by hydrogenation in the presence of a noble metal catalyst, a nickel catalyst or a copper-chromium catalyst.

12. The method according to claim 11, wherein the cleavage by hydrogenation is carried out under a hydrogen pressure of 0.2 to 15.0 MPa.

13. The method according to claim 11, wherein the cleavage by hydrogenation is carried out at 120 to 200° C. for 30 min to 5 h.

14. The method according to claim 1, wherein the cleavage of the formal protecting group of the cyclic carboxylic acid in the step C is carried out by heating a solution of the cyclic carboxylic acid in a $C_1$–$C_4$ alcohol in the presence of an acidic catalyst.

15. The method according to claim 14, wherein the acidic catalyst is at least one acid selected from the group consisting of phosphoric acid, sulfuric acid, p-toluenesulfonic acid and methanesulfonic acid.

16. The method according to claim 14, wherein the acidic acid is used in an amount of 500 ppm to 5% by weight based on the cyclic carboxylic acid.

17. The method according to claim 14, wherein the solution of the cyclic carboxylic acid is heated at 60 to 200° C. for 1 to 5 h.

* * * * *